(12) United States Patent
Bernard et al.

(10) Patent No.: US 7,176,029 B2
(45) Date of Patent: *Feb. 13, 2007

(54) CLONING AND/OR SEQUENCING VECTOR

(75) Inventors: Philippe Bernard, Brussels (BE); Philippe Gabant, Brussels (BE)

(73) Assignee: Universite Libre de Bruxelles, Brussels (BE)

( * ) Notice: Subject to any disclaimer, the term of this patent is extended or adjusted under 35 U.S.C. 154(b) by 174 days.

This patent is subject to a terminal disclaimer.

(21) Appl. No.: 10/994,208

(22) Filed: Nov. 19, 2004

(65) Prior Publication Data

US 2005/0130308 A1    Jun. 16, 2005

Related U.S. Application Data

(63) Continuation of application No. 09/634,039, filed on Aug. 8, 2000, which is a continuation of application No. 09/225,152, filed on Jan. 4, 1998, now Pat. No. 6,180,407, which is a continuation-in-part of application No. 08/379,614, filed as application No. PCT/BE93/00051 on Aug. 2, 1993, now Pat. No. 5,910,438.

(30) Foreign Application Priority Data

Jul. 31, 1992    (BE) .................................. 9200696

(51) Int. Cl.
    C12N 15/70    (2006.01)
    C12N 15/81    (2006.01)
    C12N 1/21     (2006.01)
    C12P 19/34    (2006.01)

(52) U.S. Cl. ...................... 435/471; 435/480; 435/488; 435/252.3; 435/252.33; 435/91.1

(58) Field of Classification Search .................. None
    See application file for complete search history.

(56) References Cited

U.S. PATENT DOCUMENTS

| 5,300,431 A | 4/1994 | Pierce et al. |
| 5,888,732 A | 3/1999 | Hartley et al. |
| 5,910,438 A | 6/1999 | Bernard et al. |
| 6,180,407 B1 | 1/2001 | Bernard et al. |

FOREIGN PATENT DOCUMENTS

| WO | WO 94/03616 | 2/1994 |
| WO | WO 99/58652 | 11/1999 |

OTHER PUBLICATIONS

Salmon, M. et al., "The antidote and autoregulatory functions of the F plasmid CcdA protein: a genetic and biochemical survey", 1994, Mol. Gen. Genteics, vol. 244: pp. 530-538.*

Afif, H. et al., "The ratio between CcdA and CcdB modulates the transcriptional repression of the ccd poison-antidote system", 2001, Mol. Microbiology, vol. 41: pp. 73-82.*

Bernard, P. "New ccdB positive-selection cloning vectors with kanamycin or chloramphenicol selectable markers", 1995, Gene, vol. 162: pp. 159-160.*

Kuhn, et al (1986) Positive-selection vectors utilizing lethality of the EcoRl endonuclease. Gene,44:253-263.

Bex, et al. (1983) Min-F encoded proteins: Identification of a new 10.5 kilodalton species. The EMBO Journal, 2(11):1853-1861.

Messing, et al. (1977) Filamentous coliphage M13 as a cloning vehicle: Insertion of a HindII fragment of the lac regulatory region in M13 replicative form in vitro. Proc. Natl. Acad. Sci. 74(9):3642-3646.

Norrander, et al. (1983 Construction of improved M13 vectors using oligodeoxynucleotide-directed mutagenesis. Gene, 26:101-106.

Yanisch-Perron, et al. (1985) Improved M13 phage closing vectors and host strains: Nucleotide sequence of the M13mp10 and pUC19 vectors. Gen, 33:103-110.

Gronenborn (1978) Methylation of single-stranded DNA in vitro introduces new restriction endonuclease cleavage sites. Nature, 272:375-377.

Miki, et al. (1984) Control of Cell Division by Sex Factor F in Escherichia coli. J. Mol. Biol. 174:605-625.

Miki, et al. (1984) Control of Cell Division by Sex Factor F in Escherichia coli. J. Mol. Biol. 174:627-646.

Ogura, et al. (1983) Mini-F plasmid genes that couple host cell division to plasmid proliferation. Proc. Natl. Acad. Sci. USA, 80:4784-4788.

Wang (1985) DNA Topoisomerases. Ann. Rev. Biochem. 54:665-697.

Maxwell, et al. (1986) Mechanistic aspects of DNA Topoisomerases. Advan. Protein Chem. 38:69-107.

Liu (1989) DNA Topoisomerase poisons as antitumor drugs. Annu. Rev. Biochem. 58:351-375.

Bravo, et al. (1988) Killing of Escherichia coli cells modulated by components of the stability system ParD of plasmid R1. Mol. Gen. Genet. 215:146-151.

Tsuchimoto, et al. (1988) Two Genes, pelK and peml, responsible for stable maintenance of resistance plasmid R100. J. of Bateriol., 170(4):1461-1466.

Sadler, et al. (1988) Plasmids containing many tandem copies of a synthetic lactose operator. Gene 8:279-300.

Sambrook, et al. (1989) Molecular Cloning: A Laboratory Manual. Cold Spring Harbor Laboratory Press, Cold Spring Harbor, NY, pp. 4.12,A.9-A.13.

Bahassi, et al. (1995) F plasmid CcdB killer protein: ccdB gene mutants coding for non-cytotoxic proteins which retain their regulatory functions. Molecular Microbiology 15(6):1031-1037.

(Continued)

Primary Examiner—Scott D. Priebe
Assistant Examiner—Michael Burkhart
(74) Attorney, Agent, or Firm—Knobbe, Martens, Olson and Bear, LLP

(57) ABSTRACT

A cloning and/or sequencing vector enables recombinant clones to be selected directly. The vector encodes a fusion protein which includes a protein poison.

18 Claims, 1 Drawing Sheet

OTHER PUBLICATIONS (1992) Journal of Cellular Biochemistry, Keystone Symposia on Molecular & Cellular Biology, 104.

Bernard, et al. (1991) The 41 carboxy-terminal residues of the miniF plasmid CcdA protein are sufficient to antagonize the killer activity of the CcdB protein. Mol. Gen Genet 226:297-304.

Pierce, et al. (1992) A positive selection vector for cloning high molecular weight DNA by the bacteriophage P1 system: Improved cloning efficacy. Proc. Natl. Acad. Sci. 89(6):2056-2060.

Henrich, et al. (1986) Use of the lysis gene of bateriophage ΦX174 for the construction of a positive selection of a positive selection vector. Gene 42:345-349.

Sambrook, et al. (1989) Molecular Cloning: A Laboratory Manual. Cold Spring Harbor Laboratory Press, Cold Spring Harbor, NY, pp. xi-xxxviii.

Bernard, et al. (1992) Cell Killing by the F Plasmid CodB protein involves poisoning of DNA-topoisomerase II complexes. J. Mol. Biol. 226:735-745.

Bernard (1996) Positive Selection Recombinant DNA by CcdB. Bio Techniques 21 (2)320-323.

Ioannou, et al. (1994) A new bacteriophage P1-derived vector for the propagation of large human DNA fragments. Nature Genetics 6:84-89.

Gerdes (2000) Toxin-Antitoxin modules may regulate synthesis of macromolecules during nutritional stress. Journal of Bacteriology 182:561-572.

Couturier, et al. (1998) Bacterial death by DNA gyrase poisoning. Trends in Microbiology 6(7):269-275.

Gotfredson, et al. (1998) The *Escherichia coli relBe* genes belong to a new toxin-antitoxin gene family. Molecular Microbiology 29 (4):1065-1076.

Tsushimoto, et al. (1993) Autoregulation by cooperative binding of the PemI and PemK proteins to the promoter region of the *pem* operon. 237:81-88.

Ruiz-Echevarria, et al. (1991) Structural and functional comparison between the stability systems ParD of plasmid R1 and Ccd of plasmid. F. Mol. Gen. Genet 225:355-362.

Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.

Yarmolinsky (1995) Programmed cell death in bacterial populations, Science, 267:836-837.

Smith, et al. (1997) The poison-antidote stability system of the broad-host-range *Thiobacilus ferroxidans* plasmid pTF-FC2. Molecular Microbiology 26(5):961-970.

Roberts, et al. (1994) The parDE operon of the broad-host-range plasmid RK2 specifies growth inhibition associated with plasmid loss. J. Mol. Biol. 18; 237 (1): 35-51.

Aizenman, et al. (1996) An *Escherichia coli* chromosomal "addiction module" regulated by 3', 5'—bispyrophosphate: A modayk for programmed bacterial cell death. Proc. Natl. Acad. Sci. 93:6059-6063.

Lehnherr, et al. (1993) Plasmid Addiction Genes of Bacteriophage P1: *doc*, which cause cell death on curing of prophage, and *phd*, which prevents host death when prophage is retained. J. Mol. Biol. 233:414-428.

Karoui, et al. (1983) *Ham22*, a mini-F mutation which is lethal to host cell and promotes recA-dependent induction of lambdoid prophage. The EMBO Journal. 2(11): 1863-1868.

Craine (1982) Novel Selection for Tetracycline-or Chloramphenicol- Sensitive *Escherichia coli*. J. Bacteriology 151(1):487-490.

Maloy, et al. (1981) Selection for Loss of Tetracycline Resistance by *Escherichia coli*. J. Bacteriology 145(2):1110-1112.

Bochner, et al. (1980) Positive Selection for Loss of Tetracycline Resistance. J. Bacteriology 143(2):923-933.

Nilsson, et al, (1983) An Improved Positive Selection Plasmid Vector Constructed by Oiigonucleotide Mediated Mutagenesis. Nucleic Acids Research 11(22):8019-8029.

Burns, et al. (1984) Positive Selection Vectors: A Small Plasmid Vector Useful for the Direct Selection of Sau2A-generated overlapping DNA Fragments. Gene 27:323-325.

Murphy, et al. (1991) pλZd39:A New Type of cDNA Expression Vector for Low Background, High Efficiency Directional Cloning. Nucleic Acids Research 19(12):3403-3408.

Bubeck, et al. (1993) Rapid Cloning by Homologous Recombination in vivo. Nucleic Acids Research 21(15):3601-3602.

Biswas, et al. (1993) High-Efficiency Gene Inactivation and Replacement System for Gram-Positive Bacteria. J. Bacteriology 175(11):3628-3635.

Abremski, et al. (1984) Bacteriophage P1 Site-specific Recombination, J. Bio. I. Chem. 259(3):1509-1514.

Landy (1989) Dynamic, Structural, and Regulatory Aspects of λ Site-Specific Recombination. Annu. Rev. Biochem. 58:913-949.

Boyd (1993) Turbo Cloning: A Fast, Efficient Method for Cloning PCR Products and Other Blunt-Ended DNA Fragments into Plasmids. Nucleic Acids Research 21(4):817-821.

Baubonis, et al. (1993) Genomic Targeting with Purified Cre Recombinase. Nucleic Acids Research 21(9):2025-2029.

Smith, et al. (1985) Modification and Selection of Human Interleukin 2 Produced in Insect Cells by Baculovirus Expression Vector. Natl Acad. Sci. 82:8404-8408.

Peakman, et al. (1992) Highly Efficiently Generation of Recombinant Baculoviruses by Enzymatically Mediated Site-Specific *in vitro* Recombination. Nucleic Acids Research 20(3):495-500.

Holt, et al. (1993) A Novel Phage λ Replacement Cre-lox Vector that has Automatic Subcloning Capabilities. Gene 133:95-97.

Roca, et al. (1992) A Hit-and-Run System for Targeted Genetic Manipulations in Yeast. Nucleic Acid Research 20(17):4671-4672.

Maki, et al (1992) Modulation of DNA Supercoiling Activity of *Escherichia coli* DNA Gyrase by F Plasmid. The Journal of Biological Chemistry vol. 267(17):12244-12251.

Roberts, et al. (1992) Definition of a Minimal Plasmid Stabilization System from the Broad-Host-Range Plasmid RK2. Journal of Bacteriology Dec. 1992:8119-8132.

\* cited by examiner

SEQUENCE LISTING

```
<160> NUMBER OF SEQ ID NOS: 10

<210> SEQ ID NO 1
<211> LENGTH: 306
<212> TYPE: DNA
<213> ORGANISM: Artificial Sequence
<220> FEATURE:
<223> OTHER INFORMATION: ccdB gene of plasmid F
<220> FEATURE:
<221> NAME/KEY: CDS
<222> LOCATION: (1)...(306)

<400> SEQUENCE: 1 atg cag ttt aag gtt tac acc tat aaa aga gag agc cgt tat cgt ctg       48
Met Gln Phe Lys Val Tyr Thr Tyr Lys Arg Glu Ser Arg Tyr Arg Leu
 1               5                  10                  15 ttt gtg gat gta cag agt gat att att gac acg ccc ggg cga cgg atg       96
Phe Val Asp Val Gln Ser Asp Ile Ile Asp Thr Pro Gly Arg Arg Met
                 20                  25                  30 gtg atc ccc ctg gcc agt gca cgt ctg ctg tca gat aaa gtc tcc cgt      144
Val Ile Pro Leu Ala Ser Ala Arg Leu Leu Ser Asp Lys Val Ser Arg
             35                  40                  45 gaa ctt tac ccg gtg gtg cat atc ggg gat gaa agc tgg cgc atg atg      192
Glu Leu Tyr Pro Val Val His Ile Gly Asp Glu Ser Trp Arg Met Met
         50                  55                  60 acc acc gat atg ggc agt gtg ccg gtc tcc gtt atc ggg gaa gaa gtg      240
Thr Thr Asp Met Gly Ser Val Pro Val Ser Val Ile Gly Glu Glu Val
 65                  70                  75                  80 gct gat ctc agc cac cgc gaa aat gac atc aaa aac gcc att aac ctg      288
Ala Asp Leu Ser His Arg Glu Asn Asp Ile Lys Asn Ala Ile Asn Leu
                 85                  90                  95 atg ttc tgg gga ata taa                                              306
Met Phe Trp Gly Ile *
            100

<210> SEQ ID NO 2
<211> LENGTH: 420
<212> TYPE: DNA
<213> ORGANISM: Artificial Sequence
<220> FEATURE:
<223> OTHER INFORMATION: ccdB gene of pKIL 18
<220> FEATURE:
<221> NAME/KEY: CDS
<222> LOCATION: (1)...(381)
```

<400> SEQUENCE: 2

| | | | |
|---|---|---|---|
| atg acc atg att acg aat tcg agc tcg gta ccc ggg gat cct cta gag<br>Met Thr Met Ile Thr Asn Ser Ser Ser Val Pro Gly Asp Pro Leu Glu<br>1               5                   10                  15 | | | 48 |
| tcg acc tgc agg cat gca agc ttg tct ttg cag ttt aag gtt tac acc<br>Ser Thr Cys Arg His Ala Ser Leu Ser Leu Gln Phe Lys Val Tyr Thr<br>            20                  25                  30 | | | 96 |
| tat aaa aga gag agc cgt tat cgt ctg ttt gtg gat gta cag agt gat<br>Tyr Lys Arg Glu Ser Arg Tyr Arg Leu Phe Val Asp Val Gln Ser Asp<br>        35                  40                  45 | | | 144 |
| att att gac acg ccc ggg cga cgg atg gtg atc ccc ctg gcc agt gca<br>Ile Ile Asp Thr Pro Gly Arg Arg Met Val Ile Pro Leu Ala Ser Ala<br>    50                  55                  60 | | | 192 |
| cgt ctg ctg tca gat aaa gtc tcc cgt gaa ctt tac ccg gtg gtg cat<br>Arg Leu Leu Ser Asp Lys Val Ser Arg Glu Leu Tyr Pro Val Val His<br>65                  70                  75                  80 | | | 240 |
| atc ggg gat gaa agc tgg cgc atg atg acc acc gat atg gcc agt gtg<br>Ile Gly Asp Glu Ser Trp Arg Met Met Thr Thr Asp Met Ala Ser Val<br>                85                  90                  95 | | | 288 |
| ccg gtc tcc gtt atc ggg gaa gaa gtg gct gat ctc agc cac cgc gaa<br>Pro Val Ser Val Ile Gly Glu Glu Val Ala Asp Leu Ser His Arg Glu<br>            100                 105                 110 | | | 336 |
| aat gac atc aaa aac gcc att aac ctg atg ttc tgg gga ata taa<br>Asn Asp Ile Lys Asn Ala Ile Asn Leu Met Phe Trp Gly Ile *<br>        115                 120                 125 | | | 381 |
| atgtcaggct ccgttataca caagctagct tggcactgg | | | 420 |

<210> SEQ ID NO 3
<211> LENGTH: 416
<212> TYPE: DNA
<213> ORGANISM: Artificial Sequence
<220> FEATURE:
<223> OTHER INFORMATION: ccdB gene of plasmid pKIL 19
<220> FEATURE:
<221> NAME/KEY: CDS
<222> LOCATION: (1)...(381)

<400> SEQUENCE: 3

| | | | |
|---|---|---|---|
| atg acc atg att acg cca agc ttg cat gcc tgc agg tcg act cta gag<br>Met Thr Met Ile Thr Pro Ser Leu His Ala Cys Arg Ser Thr Leu Glu<br>1               5                   10                  15 | | | 48 |
| gat ccc cgg gta ccg agc tcg aat tca ttg cag ttt aag gtt tac acc<br>Asp Pro Arg Val Pro Ser Ser Asn Ser Leu Gln Phe Lys Val Tyr Thr<br>            20                  25                  30 | | | 96 |
| tat aaa aga gag agc cgt tat cgt ctg ttt gtg gat gta cag agt gat<br>Tyr Lys Arg Glu Ser Arg Tyr Arg Leu Phe Val Asp Val Gln Ser Asp<br>        35                  40                  45 | | | 144 |
| att att gac acg ccg ggg cga cgg atg gtg atc ccc ctg gcc agt gca<br>Ile Ile Asp Thr Pro Gly Arg Arg Met Val Ile Pro Leu Ala Ser Ala<br>    50                  55                  60 | | | 192 |
| cgt ctg ctg tca gat aaa gtc tcc cgt gaa ctt tac ccg gtg gtg cat<br>Arg Leu Leu Ser Asp Lys Val Ser Arg Glu Leu Tyr Pro Val Val His<br>65                  70                  75                  80 | | | 240 |
| atc ggg gat gaa agc tgg cgc atg atg acc acc gat atg gcc agt gtg<br>Ile Gly Asp Glu Ser Trp Arg Met Met Thr Thr Asp Met Ala Ser Val<br>                85                  90                  95 | | | 288 |
| ccg gtc tcc gtt atc ggg gaa gaa gtg gct gat ctc agc cac cgc gaa<br>Pro Val Ser Val Ile Gly Glu Glu Val Ala Asp Leu Ser His Arg Glu<br>            100                 105                 110 | | | 336 |
| aat gac atc aaa aac gcc att aac ctg atg ttc tgg gga ata taa<br>Asn Asp Ile Lys Asn Ala Ile Asn Leu Met Phe Trp Gly Ile *<br>        115                 120                 125 | | | 381 |

Asn Asp Ile Lys Asn Ala Ile Asn Leu Met Phe Trp Gly Ile *
        115                 120                 125 atgtcaggct ccgttataca cgaattaatt cagtg                              416

<210> SEQ ID NO 4
<211> LENGTH: 101
<212> TYPE: PRT
<213> ORGANISM: Artificial Sequence
<220> FEATURE:
<223> OTHER INFORMATION: ccdB protein of plasmid F

<400> SEQUENCE: 4

Met Gln Phe Lys Val Tyr Thr Tyr Lys Arg Glu Ser Arg Tyr Arg Leu
1               5                   10                  15

Phe Val Asp Val Gln Ser Asp Ile Ile Asp Thr Pro Gly Arg Arg Met
            20                  25                  30

Val Ile Pro Leu Ala Ser Ala Arg Leu Leu Ser Asp Lys Val Ser Arg
        35                  40                  45

Glu Leu Tyr Pro Val Val His Ile Gly Asp Glu Ser Trp Arg Met Met
    50                  55                  60

Thr Thr Asp Met Gly Ser Val Pro Val Ser Ile Gly Glu Glu Val
65                  70                  75                  80

Ala Asp Leu Ser His Arg Glu Asn Asp Ile Lys Asn Ala Ile Asn Leu
                85                  90                  95

Met Phe Trp Gly Ile
            100

<210> SEQ ID NO 5
<211> LENGTH: 126
<212> TYPE: PRT
<213> ORGANISM: Artificial Sequence
<220> FEATURE:
<223> OTHER INFORMATION: ccdB protein of plasmid pKIL 18

<400> SEQUENCE: 5

Met Thr Met Ile Thr Asn Ser Ser Ser Val Pro Gly Asp Pro Leu Glu
1               5                   10                  15

Ser Thr Cys Arg His Ala Ser Leu Ser Leu Gln Phe Lys Val Tyr Thr
            20                  25                  30

Tyr Leu Arg Glu Ser Arg Tyr Arg Leu Phe Val Asp Val Gln Ser Asp
        35                  40                  45

Ile Ile Asp Thr Pro Glu Arg Arg Met Val Ile Pro Leu Ala Ser Ala
    50                  55                  60

Arg Leu Leu Ser Asp Lys Val Ser Arg Glu Leu Tyr Pro Val Val His
65                  70                  75                  80

Ile Gly Asp Glu Ser Trp Arg Met Met Thr Thr Asp Met Ala Ser Val
            85                  90                  95

Pro Val Ser Val Ile Gly Glu Glu Val Ala Asp Leu Ser His Arg Glu
            100                 105                 110

Asn Asp Ile Leu Asn Ala Ile Asn Leu Met Phe Trp Gly Ile
        115                 120                 125

<210> SEQ ID NO 6
<211> LENGTH: 126
<212> TYPE: PRT
<213> ORGANISM: Artificial Sequence
<220> FEATURE:
<223> OTHER INFORMATION: ccdB protein of plasmid pKIL 19

```
<400> SEQUENCE: 6

Met Thr Met Ile Thr Pro Ser Leu His Ala Cys Arg Ser Thr Leu Glu
 1               5                  10                  15

Asp Pro Arg Val Pro Ser Ser Asn Ser Leu Gln Phe Leu Val Tyr Thr
            20                  25                  30

Tyr Lys Arg Glu Ser Arg Tyr Arg Leu Phe Val Asp Val Gln Ser Asp
        35                  40                  45

Ile Ile Asp Thr Pro Gly Arg Arg Met Val Ile Pro Leu Ala Ser Ala
    50                  55                  60

Arg Leu Leu Ser Asp Lys Val Ser Arg Glu Leu Tyr Pro Val Val His
65                  70                  75                  80

Ile Gly Asp Glu Ser Tyr Arg Met Met Thr Thr Asp Met Ala Ser Val
                85                  90                  95

Pro Val Ser Val Ile Gly Glu Glu Val Ala Asp Leu Ser His Arg Glu
            100                 105                 110

Asn Asp Ile Lys Asn Ala Ile Asn Leu Met Phe Trp Gly Ile
        115                 120                 125

<210> SEQ ID NO 7
<211> LENGTH: 31
<212> TYPE: DNA
<213> ORGANISM: Artificial Sequence
<220> FEATURE:
<223> OTHER INFORMATION: kid1 primer

<400> SEQUENCE: 7
gaggaattca ttgggaaaga ggggaaatct g                              31

<210> SEQ ID NO 8
<211> LENGTH: 29
<212> TYPE: DNA
<213> ORGANISM: Artificial Sequence
<220> FEATURE:
<223> OTHER INFORMATION: kid2 primer

<400> SEQUENCE: 8
gaggaattct caagtcagaa tagtggaca                                 29

<210> SEQ ID NO 9
<211> LENGTH: 30
<212> TYPE: DNA
<213> ORGANISM: Artificial Sequence
<220> FEATURE:
<223> OTHER INFORMATION: kid3 primer

<400> SEQUENCE: 9
gagaagctta ttggaaagag gggaaatctg                                30

<210> SEQ ID NO 10
<211> LENGTH: 29
<212> TYPE: DNA
<213> ORGANISM: Artificial Sequence
<220> FEATURE:
<223> OTHER INFORMATION: kid4 primer

<400> SEQUENCE: 10
gagaagcttt caagtcagaa tagtggaca                                 29
```

CLONING AND/OR SEQUENCING VECTOR

RELATED APPLICATIONS

This application is a continuation application which claims priority under 35 U.S.C. § 120 to U.S. patent application Ser. No. 09/634,039, entitled CLONING AND/OR SEQUENCING VECTOR, filed Aug. 8, 2000, which is a continuation of U.S. patent application Ser. No. 09/225,152, entitled CLONING AND/OR SEQUENCING VECTOR, filed Jan. 4, 1998 and issued as U.S. Pat. No. 6,180,407, which is a continuation-in-part of U.S. patent application Ser. No. 08/379,614, entitled CLONING AND/OR SEQUENCING VECTOR, having a § 371(c) date of Jul. 20, 1995 and issued as U.S. Pat. No. 5,910,438, which is the U.S. National Phase under 35 U.S.C. § 371 of International Application PCT/BE93/00051, entitled CLONING AND/OR SEQUENCING VECTOR, filed Aug. 2, 1993 and published in English as PCT Publication No. WO94/03616, which claims priority to Belgian Application No. BE 9200696, filed Jul. 31, 1992.

SUBJECT-MATTER OF THE INVENTION

The invention relates to a cloning and/or sequencing vector which enables recombinant clones to be selected directly.

The invention also relates to the procaryote cell which is transformed by this vector and to the procaryote host cell for this vector, as well as to the use of this cloning and sequencing vector for selecting and sequencing recombinant clones.

State of the Art and Technological Background Underlying the Invention

Phage (the M13 series) and plasmid (the pUC series) cloning vectors, containing numerous unique cloning sites, were constructed by Messing et al (P.N.A.S. USA, 79, pp. 3642–3646 (1977), by Norrander et al (Gene, 26, pp. 101–106 (1983) and Yanisch-Perron et al (Gene, 33 pp. 103 to 119) (1985)).

The multiple cloning sites (MCS—multiple cloning sites) of these vectors are located in the coding sequence of the LacZ gene.

Discrimination between the transformed cells which harbour a recombinant vector and the cells which harbour a non-recombinant vector is achieved using the "blue screen" technique described by Gronenborn and Messing (Methylation of single-stranded DNA in vitro introduces new restriction endonuclease cleavage sites, Nature, 272, pp. 375–377 (1978)).

However, this "blue screen" technique suffers from the disadvantage of using a screening procedure (discrimination) rather than a procedure for selecting the clones.

Discrimination by screening is based on identifying a clone within a population of clones on the basis of a characteristic (color) which differentiates it. Selection has no need of this characteristic, since it is only recombinant clones which are isolated by this method.

The screening procedure is based on the color of the recombinant clones (white color) and of the non-recombinant clones (blue color). This color is based on inactivation of the marker beta-galactosidase, preventing cleavage of X-gal (5-bromo-4-chloro-3-indolyl β-galactoside). The cell colonies harbouring a non-recombinant vector produce a functional beta-galactosidase and, by hydrolysing the X-gal substrate, produce a blue coloration. In general, the insertion of a DNA fragment into the β-galactosidase gene prevents cleavage of the X-gal. For this reason, the cells harbouring a recombinant vector have a white color.

Moreover, this complex procedure requires the use of the substrate X-gal which is a product which is very expensive, unstable and awkward to use.

On the other hand, various cloning vectors permitting direct selection (positive selection) of recombinant strains have been described in the scientific literature.

Pierce et al (Proc. Natl. Acad. Sci., vol 89. No. 6, 1992, pp. 2056–2060) describe a vector which comprises the lethal gene sacB from *Bacillus* amylolique-faciens, integrated into a plasmid derived from the bacteriophage P1 and under the control of a specific *E. coli* promoter.

The promoter of this vector includes a region having several specific cloning sites (cleavage site for a restriction enzyme).

Since the gene sacB encodes levan sucrase, which catalyses the hydrolysis of sucrose into products which are toxic for *E. coli*, direct selection of the mutants which incorporate a recombinant plasmid is effected on a culture medium containing sucrose. Since the levan sucrase is toxic, even in the absence of sucrose, it is essential, consequently, to repress its synthesis if one wishes to obtain a large number of plasmid copies in the bacterial cytoplasm.

However, it is difficult, if not impossible, to repress the cytotoxic gene completely, particularly if a large number of copies of the vector are required.

Therefore, the impossibility of repressing the cytotoxic gene leads, in phases of producing the plasmid, to the death of the cell and, as a consequence, to selective pressure towards mutated strains (characterised by an inactive lethal gene).

In this case, in order to ensure that the enzyme encoded by the sacB gene does not kill the host cell, it is necessary to incorporate a CI repressor, which regulates the expression of this gene, into the cloning vector.

Furthermore, since sucrose is often incorporated into bacterial culture media, it will be essential to prepare media which are totally free of sucrose in order to carry out these manipulations.

Henrich et al (Gene, vol 42, No. 3, 1986, pp. 345–349) describe a vector which includes the E gene from the bacteriophage ΦX174, the said E gene being incorporated into the plasmid pUH84 under the control of the Lac promoter.

In this case, the E gene includes six unique restriction sites (located over the whole of the E gene sequence) and encodes gpE, which causes lysis of the *E. coli* cell. In this case, positive selection is effected when a foreign recombinant gene has been inserted into one of the restriction sites.

However, this insertion of a foreign gene into a restriction site located in the sequence of the E gene, encoding gpE, makes it more difficult to sequence the foreign gene and/or amplify it by PCR since, in this case, portions of useless sequences belonging to the E gene encoding gpE are also sequenced, amplified and characterised.

Kuhn et al (Gene, vol 42, No. 3, 1986, pp. 253–263) describe a vector which includes a large gene encoding a restriction enzyme which kills by cleaving the genome of the bacterium, the said gene being incorporated into the plasmid pKG2 under the control of the LacUV5 promoter.

The cloning vectors of the state of the art suffer from the disadvantage of having to be maintained in a host strain which includes the LacI$^q$ repressor in episomal form, or the CI repressor, in order to inactivate the promoter and prevent expression of the killer gene, leading to the death of the host strain.

In addition, if it is desired to use this strain to produce a large number of copies of the cloning vectors, the repressor will not be adequate for preventing either a selective pressure which modifies the cytotoxic activity of the vector or a "genetic leakage", that is to say expression of certain copies of the vector and death of the host strain.

Consequently, none of the documents of the state of the art describes a cloning vector which can incorporate large nucleotide fragments, which is easy to manipulate and which can be produced by a micro-organism on an industrial scale; that is to say, which can be produced in a large number of copies by a micro-organism without bringing about the death of the latter.

OBJECTS OF THE INVENTION

The present invention aims to supply a novel cloning and/or sequencing vector, and also its host strain, which are simple and relatively inexpensive to construct and produce, and which enable recombinant clones to be selected directly, without suffering from the disadvantages of the above-mentioned state of the art.

A particular object of the present invention is to obtain a vector which permits specific and certain selection of the recombinant clones.

Another object of the present invention is directed towards obtaining a vector which permits the sequencing, amplification and/or characterisation, using the same primer, of any foreign DNA fragment (whatever its size) in the recombinant clones.

An additional object of the present invention is directed towards obtaining a vector which also permits simple extraction of this foreign DNA fragment from the recombinant clone.

A final object of the present invention is directed towards obtaining a host strain for the said vector which allows a large number of copies of the said vector to be produced without bringing about selective pressure which modifies the cytotoxic activity of the said vector or causing the death of the host strain.

Characteristic Elements of the Invention

The invention relates to a novel cloning and/or sequencing vector which includes, incorporated into an autonomously replicating vector, at least one promoter nucleotide sequence and at least one nucleotide sequence encoding a fusion protein which is active as a poison, the said nucleotide sequence being obtained by fusing a coding nucleotide sequence which includes several unique cloning sites and a nucleotide sequence which encodes a protein poison.

Preferably, the autonomously replicating vector is a recombinant virus or a recombinant plasmid such as a pUC plasmid.

The promoter nucleotide sequence can comprise any promoter, which permits expression of the nucleotide sequence encoding a fusion protein which is active as a poison.

Preferably, this promoter nucleotide sequence consists of the Lac operon promoter.

According to one preferred embodiment of the invention, the unique cloning sites (MCS) of the nucleotide sequence which is fused to the nucleotide sequence which encodes the protein poison are absent from the remainder of the nucleotide sequence of the vector according to the invention.

Advantageously, the nucleotide sequence of the gene which encodes the protein poison comprises all or part of the nucleotide sequence of the wild-type gene which encodes the protein CcdB or the protein Kid.

Preferably, the nucleotide sequence of the gene which encodes the protein poison lacks the cleavage site for the restriction enzyme SmaI.

Another aspect of the invention relates to a procaryote cell which is transformed with the cloning vector according to the invention.

The invention also relates to a procaryote host cell for the vector according to the invention which possesses a chromosomal I$^q$ and an elevated transformation efficiency, and which possesses a mutation conferring resistance to the poison activity of the fusion protein, and/or which possesses a gene encoding a protein which is an antipoison to the fusion protein.

Preferably, the procaryote host cell for the vector according to the invention possesses a mutation in the gene encoding subunit A, or in the gene encoding subunit B, of the gyrase, and conferring resistance to the fusion protein, and/or a gene which encodes the protein CcdA which is an antipoison to the fusion protein comprising CcdB and/or encodes the protein Kis which is an antipoison of the fusion protein comprising Kid.

Preferentially, the procaryote cell is an *Escherichia coli* cell which possesses a mutation which is responsible for replacing arginine 462 with a cysteine in the amino acid sequence of the GyrA polypeptide of the gyrase, thereby conferring resistance to the fusion protein.

Preferably, this procaryote host cell also possesses the LacI$^q$ mutation.

The present invention also relates to fragments of the vector according to the invention, in particular primers for sequencing and/or amplifying (for example by PCR) the foreign nucleotide fragments inserted into the vector according to the invention.

Preferably, these primers consist of sequences of from 10 to 30 nucleotides which hybridise to nucleotide sequences which are situated on either side of the nucleotide sequence of the vector according to the invention which contains several unique cloning sites.

A final aspect of the invention relates to the use of the vector according to the invention for selecting and sequencing recombinant clones.

DESCRIPTION OF A PREFERRED EMBODIMENT OF THE INVENTION

Figure 1:
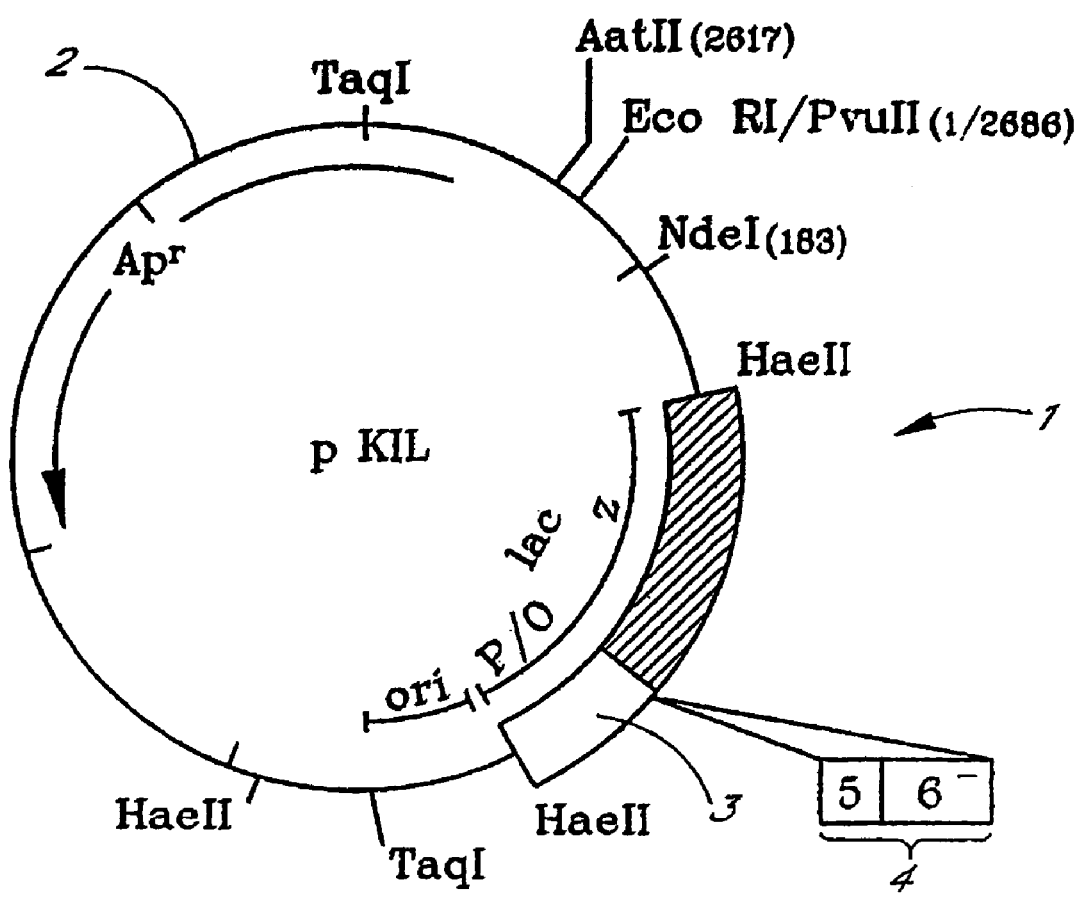
FIG. 1 is a diagrammatic representation of a cloning vector according to the present invention.

According to the invention, the cloning and/or sequencing vector 1 includes, incorporated into an autonomously replicating vector 2, at least one promoter nucleotide sequence 3 and at least one nucleotide sequence 4 which encodes a fusion protein which is active as a poison, the said nucleotide sequence 4 being obtained by fusing a coding nucleotide sequence 5 (or polylinker) which encompasses several (multiple) unique cloning sites (MCS), and a nucleotide sequence (6) which encodes a protein poison.

An autonomously replicating vector 2 is understood to mean any nucleotide construct, such as a virus or a plasmid (preferably a recombinant plasmid of the PUC series), which is capable of being introduced into a micro-organism, of recombining therein and/or of replicating therein.

FIG. 1 shows a diagrammatic representation of a cloning vector according to the present invention, which vector is constructed from a plasmid of the pUC series (pUC18 and pUC19), which is described by Norrander et al (Construction of improved M13 vectors using oligo-deoxinucleotide-directed mutagenesis, Gene, 26, pp. 101–106 (1983)) and by Yanisch-Perron et al (Improved M13 phage cloning vectors and host strains nucleotide sequences of the M13 mp18 and pUC19 vectors, Gene, 33, pp. 103–119 (1985)).

A coding nucleotide sequence 5 encompassing several (multiple) unique cloning sites (MCS) is understood to mean a short coding sequence (or polylinker) which comprises several cleavage sites for restriction enzymes.

The advantage of having a polylinker in the vector according to the invention is that different cloning sites are located on a single short sequence, thereby permitting:

rapid sequencing and amplification, using the same primers, of any DNA fragment which is inserted into this vector, rapid extraction of the cloned fragment, facilitated by the proximity of the restriction sites. Thus, in contrast to the state of the art, this proximity avoids sequencing, amplifying and characterising useless fragments from other sequences of the vector according to the invention.

Nucleotide sequence 6 encoding a protein poison is understood to mean any (wild-type) nucleotide structure encoding a protein which displays an activity which is naturally poisonous and specific for one or more vital functions of a host cell.

A protein poison is also characterised by the existence of an antidote or antipoison, such as the proteins CcdB and CcdA, the protein Kid and its antagonist Kis, the protein PemK and its antagonist PemI, the protein Doc and its antagonist Phd, the protein HoK and its antagonist Sok, and other poison molecules which are, or are not, of plasmid origin.

In this case, the nucleotide sequence 6 encoding a protein poison consists of the wild-type gene CcdB, which encodes the protein CcdB (control of cell death), obtained from the ccd locus of the F plasmid (SEQ ID NO:1 and SEQ ID NO:4).

The ccd locus of the F plasmid comprises the two wild-type genes ccdA and ccdB, also termed H and G, or letA and letD, which respectively encode proteins of 72 and 101 amino acids (Bex et al, Mini-F encoded proteins; identification of a new 10.5 kilodalton species. EMBO J. 2, 1853–1861 (1983); Miki et al, Control of cell division by sex factor F in *Escherichia coli*. I. The 42.84–43.6 F segment couples cell division of the host bacteria with replication of plasmid DNA, J. Mol. Bio., 174, 605–625, (1984)).

In *Escherichia coli*, the CcdB protein of the F plasmid is a cytotoxin whose lethal activity is counteracted by the protein CcdA (Karoui et al, Ham22, a mini-F mutation which is lethal to host cell and promotes recA-dependent induction of lambdoid prophage. EMBO J. 2, 1863–1868 (1983); Ogura and Hiraga Mini-F plasmid gene that couple host cell division to plasmid proliferation, Proc. Natl. Acad. Sci. USA, 80, 4784–4788 (1983); Miki et al, Control of cell division by sex factor F in *Escherichia coli*. Identification of genes for inhibitor protein and trigger protein on the 42.84–43.6F segment, J. Mol. Biol. 174, 627–646 (1984b)).

The molecular mechanism by which protein CcdB exerts its lethal activity has been elucidated; protein CcdB is poisonous to DNA topoisomerase II.

The type II DNA topoisomerases are essential and ubiquitous enzymes which alter the topology of the DNA by transiently introducing a double-stranded break into the DNA. During the stage of break-religation, topoisomerase II forms an intermediate complex with its DNA substrate in which the enzyme is attached covalently to the 5' end of the cleaved DNA, This transitory intermediate, in which topoisomerase II is linked covalently to the DNA, has been termed the "cleavable complex" (Wang, DNA topoisomerases. Annu. Rev. Biochem. 54, 665–97, 1985; Maxwell & Gellert, Mechanistic aspects of DNA topoisomerases. Advan. Protein Chem. 38, 69–107, 1986; Liu, DNA topoisomerase poisons as antitumor drugs, Annu. Rev. Biochem. 58, 351–375, 1989).

Both in eucaryotes and in procaryotes, the cleavable topoisomerase II-DNA complex is the target of powerful therapeutic agents, including the antibiotics of the "quinolone" family, which act on the gyrase (bacterial topoisomerase II), and anticancer agents (acridines and epipodophyllotoxins), which act on the mammalian topoisomerase II. The therapeutic efficacy of the topoisomerase poisons is correlated with their ability to stabilise the cleavable complex.

DNA topoisomerase II is an essential enzyme in all living entities and is very conserved in the evolution of the species. The CcdB protein thus displays an activity which is potentially cytotoxic for a wide variety of procaryote species.

The small size of the wild-type ccdB gene allows it to be inserted into plasmids without increasing their size excessively and consequently allows large fragments of foreign DNA to be included therein, Furthermore, given its small size, the wild-type ccdB gene of the F plasmid contains very few restriction sites; it is, therefore, simpler to preserve the uniqueness of the multiple cloning sites (MCS) which are added to it.

Unexpectedly, the inventors observed that the in-phase fusion of the nucleotide sequence 6, encoding protein CcdB, with the coding nucleotide sequence (polylinker 5), comprising several (multiple) unique cloning sites (MCS) gave a nucleotide sequence 4 which encodes a fusion protein which is active as a poison and which makes it possible, as a consequence, to produce vectors for the direct selection of recombinant plasmids (killer selection).

The plasmids which have been obtained allow doubly digested restriction fragments to be cloned in both orientations with respect to the lac promoter. Insertion of a restriction fragment into one of the unique cloning sites interrupts the genetic information of the gene fusion, leading to the synthesis of a gene fusion product which is not functional. Insertional inactivation of the gene fusion ought always to take place when a termination codon is introduced or when a change is made in the reading frame.

The cells which harbour an intact cloning vector of this nature produce a poisonous fusion protein which is functional, and die.

Insertion of a foreign DNA fragment into one of the unique cloning sites of the gene fusion interferes with production of the poison.

The cells which harbour a recombinant vector will be viable while cells which harbour an intact vector will not be viable. This killer selection, by simple culture on a solid medium, makes it possible to eliminate cells which harbour a non-recombinant vector (non-viable clones) and to select recombinant clones (viable clones).

EXAMPLE I

Construction of the Plasmid PKIL19

The ccdB gene was amplified by PCR using, as DNA template, the plasmid pULB2208 (Bernard and Couturier, The 41 carboxy-terminal residues of the miniF plasmid CcdA protein are sufficient to antagonise the killer activity of the CcdB protein, Mol. Gen. Genet. 226, 297–304 (1991) as well as synthetic oligonucleotides.

The synthetic oligonucleotide sequences were selected in such a way as to create an EcoRI restriction site on either side of the wild-type ccdB gene in order to be able to reclone this gene in frame with the codons of the MCS19 multiple cloning site and to eliminate the initiation codon of the native ccdB gene. The DNA resulting from the PCR reaction was digested with the enzyme EcoRI and cloned into the EcoRI site of the plasmid pUC19. The resulting plasmid, in which the EcoRI fragment was integrated in the orientation which permitted the ccdB gene, provided with the additional codons corresponding to the MCS19 multiple cloning sites, to be read from the Lac promoter, was termed pKIL2. Plasmid pKIL2 is lethal for a wild-type bacterium ($Ccdb^S$ sensitive).

pKIL2 also possesses two SmaI sites, one in the multiple cloning sites and the other in the central region of the ccdB gene. The latter was eliminated by site-directed mutagenesis. The resulting plasmid pKIL3, having a unique SmaI site, still has two EcoRI sites. The EcoRI site downstream of the ccdB gene was eliminated by filling in its cohesive ends.

The resulting plasmid, pKIL19 (SEQ ID NO:2 and SEQ ID NO:5), thus possesses a unique EcoRI restriction site within sequnce 5, which encompasses the multiple cloning site.

EXAMPLE II

Construction of the Plasmid pKIL18

The ccdB gene was amplified by PCR using, as DNA template, plasmid pKIL19 as well as synthetic oligonucleotides. The sequences of the synthetic oligonucleotides were selected in such a way as to create a HindIII site on either side of the ccdB gene in order to be able to reclone this gene in frame with the codons of the MCS18 multiple cloning sites. The DNA resulting from the PCR reaction was digested by the enzyme HindIII and cloned into the HindIII site of the plasmid pUC18. The resulting plasmid, in which the HindIII fragment was integrated in the orientation which permitted the ccdB gene, provided with the additional codons corresponding to the MCS18 multiple cloning sites, to be read from the Lac promoter, was termed pKIL4. Plasmid pKIL4 is lethal for a $Ccdb^S$-sensitive bacterium.

The HindIII site downstream of the ccdB gene was eliminated by filling in its cohesive ends. The resultant plasmid, pKIL18 ((SEQ ID NO:4 and SEQ ID NO:6), possesses a unique HindIII restriction site as well as a unique SmaI site (since constructed from pKIL19).

EXAMPLE III

Construction of the Plasmid pKID18

ParD is a killer stability system of R1 plasmid located in the proximity of the basic replicon. It is a small operon containing two genes, Kid and Kis, coding for a killer component and its antagonist respectively (Bravo et al., Mol. Gen. Genet., Vol. 215, pp. 146–151 (1988)). This system is perfectly conserved and functional in another incFII plasmid, R100 (pem system: Tsuchimoto et al., J. of Bacteriol., Vol. 170, pp. 1461–1466 (1988)), PemA (identical to Kis) and PemB (identical to Kid).

The vectors pKID18 and pKID19 contain the Kid gene fused to different polylinkers (MCS18 and MSC19 for pKID18 and pKID19 respectively). The Kid sequence was amplified by PCR from the plasmid R1 drd19 using the primers kid1—gaggaattcattgggaaagaggggaaatctg—(SEQ ID NO:7) and kid2—gaggaattctcaagtcagaatagtggaca—(SEQ ID NO: 8). The generated insert was cloned into the EcoRI site of pUC19 (Yanish-Perron et al. (1985)). This insertion generates a fusion gene between the MCS19 and Kid. The vector pKID18 was obtained as follows: the Kid sequence was amplified by PCR from the plasmid R1 drd19 using the primers kid3—gagaagcttattggaaagaggggaaatctg—(SEQ ID NO:9) and kid4—gagaagctttcaagtcagaatagtggaca—(SEQ ID NO:10). The generated insert was cloned into the HindIII site of pUC18 (Yanish-Perron et al. (1985)). This insertion generates a fusion gene between the MCS18 and Kid.

In induce conditions (induction of the pLac) that control the fuse Kid transcription of this construct for the *E. coli* strain (Top-10 F Invitrogen), this vector which contains the Kid gene fused to different polylinkers has retained the poison activity of the original Kid protein.

The regulation and the expression of this vector in a specific cell which is not killed by the poison activity of the fusion protein can be obtained by a control of the promoter activity of said vector or can be obtained by the production of said vector in a cell expressing the Kis protein which is the antidote of the Kid protein.

EXAMPLE IV

Construction of the Strains $Ccdb^r$ and $Ccdb^S$

In order to be able to maintain plasmids pKIL18 and pKIL19 within a bacterium, the latter has to be resistant to the lethal effect of the fusion protein which is active as a poison, Unexpectedly, the chromosomal mutation gyrA462 confers on the strains total resistance to the poisonous effect of the fusion protein.

Moreover, since plasmids pKIL18 and pKIL19 derive directly from plasmids pUC18 and pUC19 and express the ccdB genes from the Lac promoter, it is preferable to maintain these plasmids in a $LacI^q$ strain. Thus, while, in our case, continuous overexpression of these genes does not exert a selection pressure in favour of certain mutations, the $LacI^q$ strain allows expression from the Lac promoter to be reduced and conserves the bacterial machinery, thereby guaranteeing a rapid generation time (increased production of the vector by the strain).

The strain D1210 (Sadler et al Gene 8, pp. 279–300 (1980)), derived from the strain HB101 $LacI^q$, $LacY^+$ (Maniatis et al Molecular Cloning Laboratories Man. Cold Spring Harbour Laboratory N.Y.), and characterised by a chromosomal $I^q$ and increased transformation efficiency, was transformed with the plasmid pCOS2.1. This plasmid, which confers resistance to kanamycin, carries the recA gene from *Erwinia chrysanthemi* 3665 and allows recombination in *E. coli*. A lysate of P1 phage was prepared on a Ccdb$^R$ gyrA462, zei298::Tn10 strain and used to infect the strain D1210/pCOS2.1. The transductants which were resistant to tetracycline were selected and tested for their resistance or sensitivity to the CcdB protein. One of the Ccdb$^R$ transductants was then cured of plasmid pCOS2.1 and termed KIB22.

Strain KI322 constitutes an ideal host strain for plasmids pKIL18 and pKIL19 while strain D1210 constitutes the ideal host for selecting recombinant plasmids.

Thus, strain KIB22 advantageously possesses an elevated efficiency of DNA extraction (comparable to the yield of the pUC plasmids) and, unexpectedly, resistance to the fusion protein which is encoded by pKIL18 and pKIL19.

Consequently, it is possible to use this micro-organism to produce the cloning vector according to the invention on an industrial scale in numerous copies without causing the death of the said micro-organism.

The selection is carried out simply by spreading the bacteria on a medium containing IPTG (Isopropyl-β-D-thiogalactopyranoside) as well as ampicillin.

Strain KIB22 was deposited with the Laboratorium voor Microbiologie-Bacteriënverzameling (LMG) [Microbiological Laboratory—Bacterial Collection] of the Belgian Coordinated Collections of Microorganisms (BCCM) under No. LMG P-12601.

The cloning vector pKIL19 was deposited with the Laboratorium voor Moleculaire Biologie-Plasmiden Collectie (LMBP) [Molecular Biological Laboratory-Plasmid Collection] of the Belgian Coordinated Collections of Microorganisms (BCCM) under the No. LMBP 2781.

These depositions were made in accordance with the provisions of the Budapest Treaty regarding the International Recognition of the Deposition of Microorganisms.

What is claimed is:

1. A method for propagating a cloning or sequencing vector that lacks an insert, said method comprising:
   introducing said vector into a first prokaryotic cell, said cloning vector comprising a promoter operably linked to a nucleotide sequence encoding a CcdB poison protein, said cell expressing a CcdA antidote protein;
   propagating said vector in said first prokaryotic cell, thereby expressing said CcdB poison protein without killing the cell; and
   recovering the vector.

2. The method of claim 1, further comprising introducing the vector lacking a nucleic acid insert into a second prokaryotic cell, said second prokaryotic cell being susceptible to said CcdB poison protein, thereby preventing growth of said second prokaryotic cell.

3. The method of claim 1, wherein said first prokaryotic cell comprises a mutation at amino acid position 462 of *Escherichia coli* GyrA.

4. The method of claim 3, wherein the mutation at amino acid position 462 of *E. coli* GyrA comprises replacement of arginine with a cysteine.

5. The method of claim 1, wherein said vector comprises an origin of replication from the pUC series of plasmids.

6. The method of claim 5, wherein said origin of replication is the origin of replication from pUC18 or pUC19.

7. A method of growing prokaryotic cells that comprise a cloning vector expressing a CcdB poison protein without selecting for prokaryotic cells containing mutations in the ccdB gene, comprising:
   providing the prokaryotic cells with a gene encoding a CcdA antidote protein so as to antagonize the activity of the CcdB poison protein
   providing said cells with a gene encoding *E. coli* GyrA having a mutation at amino acid position 462; and
   growing said cells while expressing the CcdB poison protein.

8. The method of claim 7, wherein the mutation at amino acid position 462 of GyrA comprises replacement of arginine with cysteine.

9. A method of growing prokaryotic cells that comprise a cloning vector encoding a CcdB poison protein comprising:
   providing said prokaryotic cells with a cloning vector with a pUC origin of replication, said cloning vector also encoding the CcdB poison protein; and
   providing said prokaryotic cells with *E. coli* GyrA having a mutation at amino acid position 462.

10. The method of claim 9, wherein the mutation at amino acid position 462 of GyrA comprises replacement of arginine with cysteine.

11. The method of claim 9, wherein said pUC origin of replication is the origin of replication from pUC 18 or pUC 19.

12. A method for propagating a cloning or sequencing vector that lacks an insert, said method comprising:
   introducing said vector into a first prokaryotic cell, said cloning vector comprising a promoter operably linked to a nucleotide sequence encoding a CcdB poison protein, said cell expressing a polypeptide consisting of the 41-carboxy terminal amino acids of a CcdA antidote protein;
   propagating said vector in said first prokaryotic cell, thereby expressing the CcdB poison protein without killing the cell; and
   recovering the vector.

13. The method of claim 12 further comprising introducing the vector lacking a nucleic acid insert into a second prokaryotic cell, said second prokaryotic cell being susceptible to the CcdB poison protein, thereby preventing growth of said second prokaryotic cell.

14. The method of claim 12, wherein said first prokaryotic cell comprises a mutation at amino acid position 462 of *E. coli* GyrA.

15. The method of claim 14, wherein the mutation at amino acid position 462 of GyrA comprises replacement of arginine with a cysteine.

16. The method of claim 12, wherein said vector comprises an origin of replication from the pUC series of plasmids.

17. The method of claim 16, wherein said origin of replication is the origin of replication from pUC 18 or pUC 19.

18. The method of claim 12, wherein said vector comprises said nucleic acid encoding the CcdB poison protein and a nucleic acid encoding the 41-carboxy terminal amino acids of the CcdA antidote protein.

* * * * *

UNITED STATES PATENT AND TRADEMARK OFFICE
CERTIFICATE OF CORRECTION

PATENT NO.         : 7,176,029 B2
APPLICATION NO. : 10/994208
DATED              : February 13, 2007
INVENTOR(S)        : Bernard et al.

It is certified that error appears in the above-identified patent and that said Letters Patent is hereby corrected as shown below:

Column 17, line 4 to 5, which reads, "said cloning vector", should read -- said vector --

Column 17, line 33, which reads, "protein", should read, -- protein; --

Column 18, line 11 to 12, which reads, "said cloning vector", should read -- said vector --

Signed and Sealed this

Ninth Day of December, 2008

JON W. DUDAS
*Director of the United States Patent and Trademark Office*